United States Patent [19]

Handrick et al.

[11] 3,979,448
[45] Sept. 7, 1976

[54] PROCESSES FOR THE CONTINUOUS PRODUCTION OF AROMATIC CARBOXYLIC ACIDS BY OXIDATION WITH NITRIC ACID OF AROMATIC COMPOUNDS CONTAINING OXIDIZABLE ACYCLIC SUBSTITUENTS

[75] Inventors: Kurt Handrick, Essen; Anton Benning, Saarbrucken; Dietrich George, Essen; Jürgen Schlegel, Iddensen, all of Germany

[73] Assignee: Bergwerksverband GmbH, Essen, Germany

[22] Filed: June 11, 1974

[21] Appl. No.: 478,395

[30] Foreign Application Priority Data

June 19, 1973 Germany............................ 2331082

[52] U.S. Cl............................ 260/524 N; 260/523 A
[51] Int. Cl.² .......................................... C07C 51/33
[58] Field of Search..................... 260/524 N, 523 A

[56] References Cited
FOREIGN PATENTS OR APPLICATIONS

| | | | |
|---|---|---|---|
| 1,418,038 | 11/1957 | Germany ........................ | 260/524 N |
| 1,258,859 | 1/1968 | Germany ........................ | 260/524 N |
| 166,671 | 1/1964 | U.S.S.R........................... | 260/524 N |
| 187,768 | 5/1965 | U.S.S.R........................... | 260/524 N |

*Primary Examiner*—Lewis Gotts
*Assistant Examiner*—D. R. Phillips
*Attorney, Agent, or Firm*—Michael J. Striker

[57] ABSTRACT

Processes for the continuous production of aromatic carboxylic acids by reaction of nitric acid with an aromatic compound having an oxidizable alkyl or alkoxyalkyl substitutent which comprise mixing the aromatic compound in the form of small droplets with a large volume of dilute nitric acid having a concentration between 2 and 14% by weight of nitric acid that is maintained at a superatmospheric pressure between 15 and 80 atmospheres and at a temperature between 160° and 230°C, which processes comprise continuously passing a reaction mixture consisting of the aromatic compound and the dilute nitric acid through a series of at least three consecutively arranged vertical reactor column in each of which the ratio of the weight of the reaction mixture containing the dilute nitric acid to the weight of the aromatic compound is continuously maintained at at least 50:1, the nitric acid concentration in each of the reactor column being continuously maintained at an originally preselected concentration by the addition of amounts of more-concentrated nitric acid while aliquot portions of the aromatic compound based upon the number of vertical reactor columns in the series are continuously introduced into each of the reactor columns, the reaction zones each being maintained at an optimal oxidation temperature between 160 and 230°C for the aromatic compound that is being oxidized, and continuously passing the reaction mixture into a final reactor column that is maintained at a higher temperature than the preceding series of reactor columns, and continuously discharging the reaction mixture containing between 10 and 20% by weight of the aromatic carboxylic acid thus produced from the final reactor column.

1 Claim, 2 Drawing Figures

PROCESSES FOR THE CONTINUOUS PRODUCTION OF AROMATIC CARBOXYLIC ACIDS BY OXIDATION WITH NITRIC ACID OF AROMATIC COMPOUNDS CONTAINING OXIDIZABLE ACYCLIC SUBSTITUENTS

INTRODUCTION

The present invention pertains to processes for the continuous production of aromatic carboxylic acids by oxidation with nitric acid of aromatic compounds having oxidizable acyclic substituents.

The oxidation processes of the present invention are particularly adapted to the oxidation of aromatic compounds having acyclic substituents that are oxidizable to aromatic carboxylic acids with nitric acid at a superatmospheric pressure. Such aromatic compounds include 1. alkyl-substituted benzenes, especially methylbenzene (toluene) and polymethylbenzenes such as the xylenes, trimethylbenzenes and tetramethylbenzenes, and alkylbenzenes having side chains such as ethylbenzene and isopropylbenzene, ethylbenzenes and isopropylbenzenes having further methyl, ethyl or isopropyl substituents, 2. alkyl-substituted diphenyls, diphenyl ethers, and diphenylmethanes, the alkyl substituents of which have at most 3 carbon atoms, 3. (methoxymethyl)-substituted benzenes such as (methoxymethyl)benzene which is also known as methyl benzyl ether, and 4. chloro-substituted, nitro-substituted and carboxy-substituted derivatives of each of the foregoing.

For lack of a better generic term, these aromatic compounds having acyclic substituents which are oxidizable to produce an aromatic carboxylic acid will be referred to in the description that follows simply as "aromatic compounds" and that term, unless further qualified, is to be understood to be restricted to aromatic compounds such as are included in the foregoing definition.

In a generic sense such aromatic compounds are benzenes, diphenyls, diphenyl oxides, and diphenylmethanes which have at least one oxidizable alkyl or alkoxyalkyl substituent, the alkyl moiety of which has at most 3 carbon atoms. These aromatic compounds may have further halo, nitro, or carboxyl substituents which are not affected by nitric acid.

BACKGROUND OF THE INVENTION

When aromatic compounds such as those defined hereinbefore are oxidized with nitric acid, the oxidation is generally conducted in vertical reactor columns.

In such oxidation reactions, it is necessary that the nitric acid and aromatic compound be intimately mixed and that, after passing through the column, the oxidation has progressed either to the final stage or to a stage at which intermediate products which are soluble in hot nitric acid are obtained. This applies especially to that portion of the aromatic compound that is present in the form of vapor in the bubbles of the waste gases and is carried along with such bubbles at a high speed upwardly in the reactor column.

A continuous process is described in U.S. Pat. No. 3,165,548 and German Patent No. 1,119,842 for the production of aromatic carboxylic acids by oxidizing a compound having an aromatic nucleus and an oxidizable side chain or acyclic substituent with nitric acid containing between 10 and 40% by weight of nitric acid at a temperature between 150° and 400°C and a superatmospheric pressure between 10 and 150 atmospheres in which the aromatic compound that is to be oxidized is premixed with the nitric acid at a temperature below the oxidation temperature and the mixture is then passed in turbulent flow into the lower end of a vertical elongated reaction zone filled with the reaction mixture and maintained adiabatically at the said oxidation temperature and pressure, the velocity of flow of the said reaction mixture decreasing to at least one-third of its original rate upon entry into the said reaction zone so as to form a vortex with the hot reaction product that is sucked back to the point of entry of the said reaction mixture, while avoiding a gas space at the upper end of the said reaction zone, and withdrawing the resulting aromatic carboxylic acid at the upper end of the said reaction zone.

An improvement of the foregoing process is described in U.S. Pat. No. 3,271,445 and German Patent No. 1,443,435 in which between 30 and 60% by weight of the nitric acid that is to be used is introduced into the reaction zone from the bottom or lower end of the reaction zone and between 40 and 60% by weight into the middle third of the reaction zone.

However, it is to be noted that the process is described in these patents as being carried out in a tantalum-lined reactor. Furthermore, the yields of aromatic carboxylic acid are unsatisfactory and the losses of nitric acid are unusually high.

In German Patent No. 1,268,131 and United Kingdom Patent No. 1,149,321 is described a process for the continuous production of trimellitic acid by oxidation of 1,2,4-trimethylbenzene (pseudocumene) in which the 1,2,4-trimethylbenzene in the form of mechanically produced globules or droplets is introduced upwardly into the lower end of a pressurized vertical reactor column containing nitric acid having a concentration between approximately 4 and approximately 14% by weight of nitric acid that had been heated to a temperature between 160° and 180°C. The reaction mixture after passing through the column is passed also upwardly from its lower end into a subsequent reactor column containing nitric acid in which the oxidation is carried to completion at a temperature between 200° and 210°C. The waste gases that are formed in both columns are each withdrawn at the tops of each column. In this process, concentrated nitric acid is introduced into the reactor columns to increase the concentration of the nitric acid in the reaction mixture that is flowing therethrough.

It has however been found that, in order to scale-up the size of the columns for commercial production, it is not practical to simply increase the dimensions of a pilot model correspondingly. Another disadvantage of the process that is described in German Patent No. 1,268,131 is that, when the aromatic compound that is to be oxidized is brought into contact with an inadequate quantity of dilute nitric acid, even in the first stage of the oxidation, a momentary deficiency of the oxidizing agent is created. This deficiency cannot be compensated for in an ideal manner by supplying more-concentrated nitric acid to the principal reaction zone, and it is not possible to locate the regions in the columns at which such momentary demands for oxidizing agent occur at the moment they occur. The nitric acid concentration is accordingly directly subject to constant fluctuations, as a result of which the oxidation product is obtained in lower yield than is expected. Furthermore, the oxidation reaction may proceed in competition with undesirable nitration reactions of the aromatic nucleus. 1,2,4-Trimethylbenzene, for example, is susceptible to such nitration reactions. substantial losses of yield of the desired aromatic carboxylic acid result from such nitration reactions and nitric acid is needlessly consumed in such reactions.

SUMMARY OF THE INVENTION

The principal object of the present invention is to provide an improved process for the continuous production of aromatic carboxylic acids by oxidation of large quantities of aromatic compounds having oxidizable acyclic substituents with nitric acid under superatmospheric pressure and optimal oxidation conditions while obtaining maximum utilization and control of the exothermic heat that is generated during the oxidation.

The foregoing object is achieved in the processes of the present invention by conducting the oxidation in a series of at least 3 and preferably from 5 to 10 successive interconnected vertical reactor columns to each of which the reaction mixture containing nitric acid is successively passed and into each of which aliquot portions of the aromatic compound that is to be oxidized are charged, the said aliquot portions being based upon the number of columns in the series, while the amount of nitric acid that is present in the reaction mixture of each of the reactor columns is maintained at a ratio by weight of at least 50:1 and preferably between 100:1 and 200:1 with respect to the aliquot portion of the aromatic compound that is charged into the particular column. The optimal temperature that is required for the oxidation reaction is maintained in the columns. Concentrated nitric acid is charged into the reaction mixture before it is passed into the successive reactor column of the series and the reaction mixture is subsequently passed into a final reactor column from which the reaction mixture which contains from about 10 to 20% by weight of the aromatic carboxylic acid that is produced in the process, is discharged. To obtain complete oxidation, it has been found to be advantageous to permit the reaction mixture to remain in the final reactor column for a period of from about 10 to 60 minutes at a temperature that is higher than the temperature that was maintained in the prior reactor columns of the series.

It was also found that, although it is desirable to distribute the aromatic compound that is to be oxidized in the form of small droplets to increase its surface area, it is necessary to avoid a sudden decrease of the concentration of the nitric acid. Therefore, the amount of nitric acid that is used in comparison with the amount of the aromatic compound that is to be oxidized is so selected that its concentration remains with a narrow selected range. The effect of the nitric acid concentration upon the yield of aromatic carboxylic acid is shown graphically in FIG. 2 of the accompanying drawings and is described in greater detail hereinafter following the Examples.

The small globules or droplets of the aromatic compound that are required in the process of the present invention can be advantageously produced by forcing or spraying the aromatic compound through capillary apertures or perforations having a diameter between 0.2 and 2.0 millimeters, and preferably between 0.6 and 1.5 millimeters, in discs or spargers which are provided in the conduits at the inlets to each of the reactor columns through which the aromatic compound is charged or introduced. Although the optimal sizes of the globules or droplets of liquid aromatic compounds, or of solid aromatic compounds which will preferably be supplied in molten form, vary within the specified range, the optimal diameter of the capilliary apertures or perforations must be determined preliminarily for each aromatic compound unless is has already been previously established.

Reactor columns constructed both of chromium-nickel steel and titanium proved to be entirely satisfactory for use in carrying out the processes of the present invention.

Despite the relatively low nitric acid concentrations and low initial temperatures that are used in the processes of the present invention, the aromatic compound was found to be unexpectedly converted during the course of a few minutes to an intermediate product that is soluble in nitric acid. As a consequence, none of the aromatic compound that is to be oxidized will be present in the manifold in which the waste gases are collected if the reaction mixture is passed through the reactor columns at a speed that is suitably controlled or adjusted. The upwardly rising stream of the waste-gas bubbles in which the vaporized aromatic compound would be carried under the pressures existing during the operation of the process has a high velocity which, at a superatmospheric pressure of 20 atmospheres, is about 0.2 meter per second. Consequently the reactor columns must have a height between about 12 and 15 meters in order to provide for a sufficiently long period of dwell or residence of the waste-gas bubbles therein and convert those portions of the aromatic compound that is introduced into the column into an intermediate compound that is soluble in the nitric acid and thereby prevent the aromatic compound from passing as such into the manifold with the waste gases.

In particular cases it has proved advantageous to introduce the aromatic compound into the reactor column in the form of an aqueous emulsion prepared with the aid of an ionic or nonionic surfactant. This is especially desirable in the case of aromatic compounds such as paraxylene which reacts sluggishly in the first stage of the oxidation. Surfactants or emulsifying agents that are particularly useful for this purpose are compounds which are not sulfonates and do not have an aromatic nucleus such as condensation products of ethylene oxide or propylene oxide or mixtures of ethylene oxide and propylene oxide with long-chain primary aliphatic alcohols.

The quantity of the waste gases in the reactor columns is dependent upon the quantity of the nitrogen oxides that are formed during the oxidation, which is also determined by the temperature and pressure at which the process is conducted. The quantity of the waste gases increases with the number of alkyl substituents or side chains of the aromatic compounds that are oxidized and further by the extent of the oxidation within each of the individual reactor columns in the series. In general, a further oxidation even takes place at the higher temperature prevailing in the final reactor column after the reaction mixture has passed through the preceding series of reactor columns. It has further proved to be advantageous to keep the volume of the waste gases that are present in the reaction mixture in the reactor columns, including the final reactor column, from exceeding an amount equivalent to about 7% by volume of the reaction mixture. By thus restricting the amount of the waste gases in the reaction mixture in the reactor columns, flow of the reaction mixture therethrough will continue as laminar and not change to a turbulent flow which would occur were the percentage of the waste gas in the mixture to be greater than this amount.

In order to keep the evaporating costs to a minimum, the continuous oxidation process of the present invention is conducted in such a manner that the reaction mixture that is discharged from the final reactor column is cooled, the precipitated aromatic carboxylic acid is separated therefrom by filtration, and from 50 to 80% of the filtrate is recirculated after being fortified by the addition of sufficient concentrated nitric acid thereto to restore it to its original initial concentration. Since the amount of nitric acid which has thus been restored to its original initial concentration is not sufficient to supply the entire amount of dilute nitric acid that is required at the start of the process, additional quantities of fresh dilute nitric acid must accordingly be introduced as well. However, only the remaining 20 to 50% of the filtrate that is not thus fortified need be evaporated for recovery of the nitric acid therefrom.

DETAILED DESCRIPTION AND PREFERRED EMBODIMENTS OF THE INVENTION

The processes of the present invention are further described in connection with the Examples which follow which were selected solely for purposes of illustration and accordingly are to be understood as not restrictive of either the invention or its scope. Alterations and modifications may accordingly be made to adapt the processes of the present invention to the oxidation of other aromatic compounds to produce aromatic carboxylic acids in accordance with the teachings herein.

EXAMPLE 1

Figure 1:
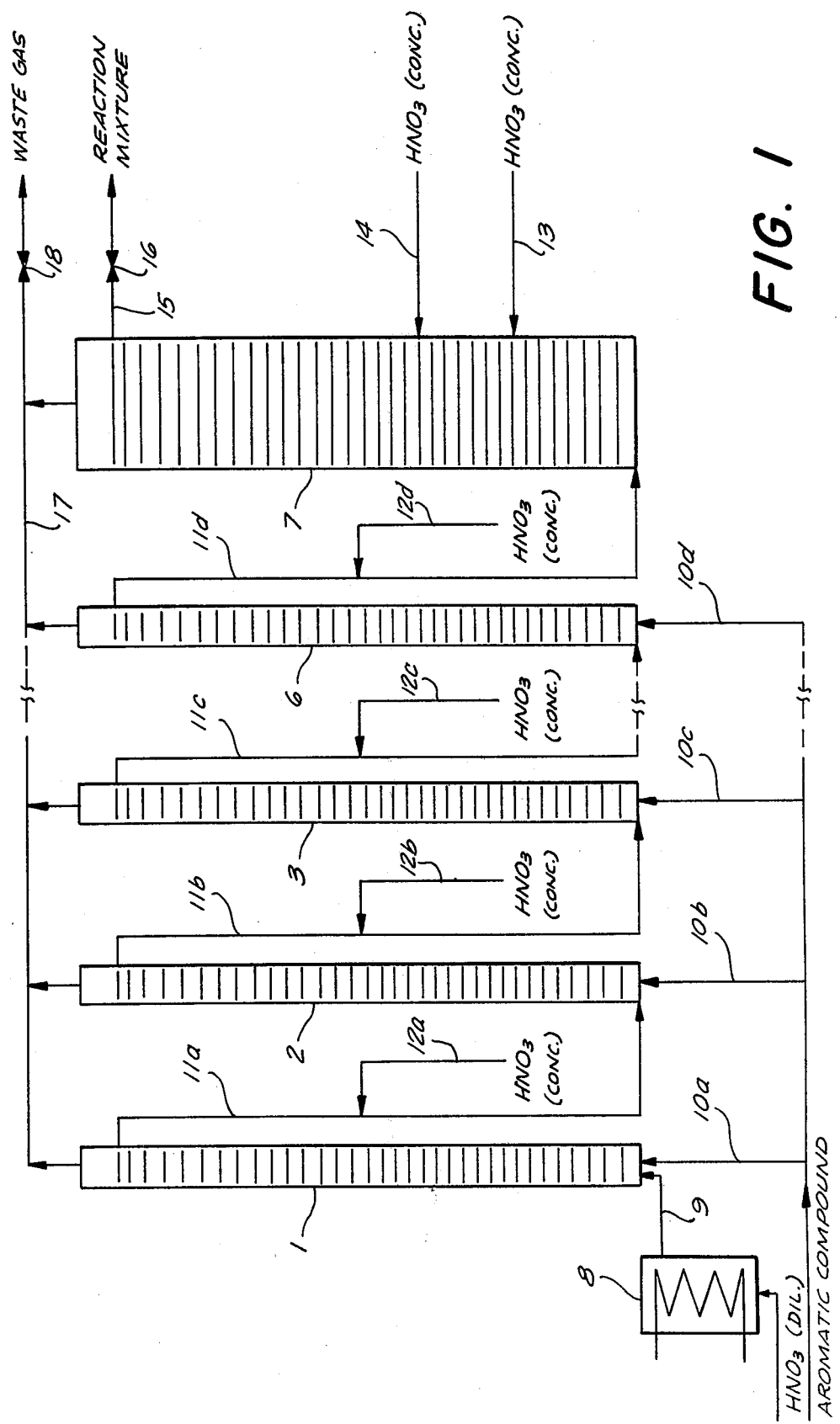
FIG. 1 of the drawings is a diagram in the form of a flow sheet of the processes of the present invention.

In FIG. 1 of the drawings is represented an oxidation apparatus such as was used in this Example which comprises six consecutive reactor columns 1 to 6, of which columns 4 and 5 are omitted in the drawing, each of which columns had a height of 12 meters and an internal diameter of 0.16 meter, and a final reactor column 7 which also had a height of 12 meters but whose internal diameter was 0.34 meter. Each of the columns 1 to 7 was heated externally by steam that was circulated through external heating jackets which are not shown in the drawing.

A dilute nitric acid solution having a specific gravity of 1.04 containing approximately 7.3% by weight of nitric acid ($HNO_3$) was heated in a tank or boiler 8 to a temperature of 175°C from which it was passed continuously into the reactor column 1 at its bottom inlet through a conduit or pipe 9 at the rate of 1200 liters per hour. During the operation of the process the contents of the reactor columns 1 to 6 were maintained at a temperature of 180°C and the temperature of the contents of the final reactor column 7 was maintained at 210°C by regulation of the circulation of steam through the external heating jackets.

When all of the columns had been filled with the dilute nitric acid at the specified temperature, 1,2,4-trimethylbenzene having a purity of 98.5% was charged into the bottom of the first of the reactor columns 1, through a conduit 10a which was provided with a sparger or perforated disc (not shown) at its outlet end. The perforations or capilliary apertures of the sparger or disc had a diameter of 0.8 millimeter. The 1,2,4-trimethylbenzene was charged into the reactor column 1, which was maintained at a super-atmospheric pressure of 22 atmospheres that was developed autogenously, at the rate of 12 kilograms per hour. After about one hour a sample of the liquid reaction mixture was withdrawn at the head of the reactor column 1 and the concentration of the nitric acid therein was determined. At that time the liquid had a specific gravity of 1.03 and contained 5.5% by weight of nitric acid. Into the conduit 11a through which the liquid at the head of reactor column 1 was passed into the bottom of reactor column 2, was charged, by means of a conduit 12a, concentrated nitric acid having a specific gravity of 1.33 and containing 52% by weight of nitric acid at a rate of 33 liters per hour, as a result of which the concentration of the nitric acid passing through the conduit 11a into the reactor column 2 was restored to its original concentration of 7.3% by weight of nitric acid having a specific gravity of 1.04. Subsequently 1,2,4-trimethylbenzene was charged into reactor column 3 through a conduit 10c which was also provided with a sparger identical with that in column 11a at the rate of 12 kilograms per hour.

In the same manner as described hereinbefore in connection with the reactor column 2, concentrated nitric acid was charged into each of the conduits 11b, 11c, and 11d connecting each of the reactor columns 3 to 6 to the next consecutive column, at the same rate as specified hereinbefore while 1,2,4-trimethylbenzene was charged at the bottom or lower end of each of the reactor columns 3 to 6 at the same rate as specified hereinbefore with respect to reactor columns 1 and 2.

The liquid reaction mixture from the last of the six reactor columns 1 to 6 was then passed from reactor column 6 through conduit 11d into the final reactor column 7 into which at two further regions of the column at distances of approximately 3 and 6 meters, respectively, from the bottom of the column, concentrated nitric acid having a specific gravity of 1.33 and containing 52% by weight of nitric acid was charged continuously through conduit 13 and 14 at a rate of 33 liters per hour to increase the nitric acid concentration of the reaction mixture in the final reactor column 7.

The reaction mixture was continuously withdrawn from the final reactor column 7 through conduit 15 while the pressure therein was released by means of a pressure-reducing valve 16, as a result of which a portion of the dilute nitric acid was vaporized. The waste gases from each of the reactor columns 1 to 6 and the final reactor column 7 were collected in a common manifold 17 and the pressure under which the gases were confined therein was released by means of a pressure-reducing valve 18.

Approximately 1250 liters of the reaction mixture, which was then cooled to a temperature of 20°C, was thus discharged hourly from the final reactor column 7 and the trimellitic acid crystals that had precipitated therein were separated from the liquid portion of the reaction mixture by centrifugation. About two-thirds of the liquid from which the trimellitic acid crystals had thus been separated were then fortified by the addition thereto of concentrated nitric acid to increase its concentration to 7.3% by weight and this liquid was recycled to the tank or boiler 8 and charged together with fresh quantities of dilute nitric acid into the reactor column 1. The remaining one-third of the liquid from which the trimellitic acid crystals had been separated was evaporated and the nitric acid was thus recovered therefrom.

After equilibrium had been established in the oxidation apparatus, 106.1 kilograms of trimellitic acid which had an acid number of 795 (theoretical is 801), equivalent to a yield of 84.2% of the theoretical, was produced hourly. The residue left after evaporation amounted to 14.5 kilograms per hour which, calculated as trimellitic acid, was equivalent to 11.5% of the theoretical yield. The residue consisted of 25% by weight of the trimellitic acid together with smaller amounts of picric acid, nitrotrimellitic aicd, nitrophthalic acids, and other by-products.

EXAMPLE 2

An emulsion was prepared by mixing together with the aid of a high-speed stirrer and an alkylated fatty oil emulsifying agent, equal parts by weight of water and paraxylene having a purity in excess of 99%. The same oxidation apparatus which is represented in FIG. 1 of the drawings that was used and described in connection with Example 1 was used in this example. Into this apparatus was charged hourly 1800 liters of heated dilute nitric acid having a specific gravity of 1.030 and a nitric acid content of 5.5% by weight. The liquid in the six reactor columns 1 to 6 was maintained at a temperature of 170°C and that in the final reactor column 7 at a temperature of 210°C, while a superatmospheric pressure of 22 atmospheres that was developed autogenously was maintained in the reactor columns. The conduit 11d leading into the final reactor column 7 was connected to the head instead of to the bottom of reactor column 7 so that the liquid therein passed therethrough from top to bottom and the reaction mixture was withdrawn through conduit 15 that was connected to the bottom of the column 7. The conduits 11a, 11b, 11c and 11d which connect each of the reactor columns to each other were also heated to prevent the formation of deposits of the terephthalic acid that was produced in the apparatus. Into each reactor column 1 to 6, 34 liters, equivalent to 15 kilograms of the emulsified paraxylene, was charged hourly while 28 liters of preliminarily heated concentrated nitric acid having a specific gravity of 1.33 and containing 52% by weight of nitric acid was charged hourly into each of the conduits 11a, 11b, 11c and 11d that interconnected the reactor columns 1 to 7 with each other.

Concentrated nitric acid having the same specific gravity and nitric acid content was charged into the final reactor column 7 through each of two conduits 13 and 14 which, however, were located at a height of 6 and 9 meters, respectively, from the bottom of the column. Concentrated nitric acid at the rate of 50 liters per hour was charged into the final reactor column 7 through each of the conduits 13 and 14.

The reaction mixture was continuously withdrawn and cooled and the pressure was released exactly as described in Example 1 hereinbefore and the terephthalic acid that was produced was recovered from the resulting reaction mixture by suction filtration.

Approximately two-thirds of the filtrate was fortified by addition of concentrated nitric acid to increase its concentration of nitric acid to 5.5% by weight and this fortified nitric acid was then recycled as described hereinbefore in connection with Example 1 and the remaining one-third of the filtrate was evaporated to recover the nitric acid therein.

In this manner, 127.5 kilograms of terephthalic acid having an acid number of 672 (theoretical is 675), equivalent to 90.5% of the theoretical yield, was produced hourly, together with 6.4 kilograms of residue which, calculated as terephthalic acid, was equivalent to 4.5% of the theoretical yield. The residue consisted of a mixture of terephthalic acid and by-products.

EXAMPLE 3

In this Example the same oxidation apparatus was used that was described hereinbefore in connection with Example 1, except that the perforations or capillary apertures in the spargers had a diameter of 1.2 millimeters and the substance that was to be oxidized, namely, durene (1,2,4,5-tetramethylbenzene), of 98% purity, was charged from a melting tank into the reactor columns 1 to 6 in molten form.

The dilute nitric acid that was used had a specific gravity of 1.06 and a nitric acid content of 10.5% by weight and it was preheated to a temperature of 170°C. The reaction mixture in each of the columns 1 to 6 was maintained at 170°C while a temperature of 200°C was maintained in the final reactor column 7. The durene which had a purity of 98% was melted in the melting tank and maintained therein at a temperature of 110°C. It was charged from the melting tank into each of the six reactor columns 1 to 6 at a rate of 10 kilograms per hour. Concentrated nitric acid having a specific gravity of 1.33 and containing 52% by weight of nitric acid was charged into each of the six conduits 11a to 11d at the rate of 30 liters per hour and at the same rate also into each of the two conduits 13 and 14 leading into the final reactor column 7, which conduits were located at heights of 3 and 6 meters, respectively, from the bottom of the column.

The pyromellitic acid (1,2,4,5-benzenetetracarboxylic acid) that was thus produced was recovered in the same manner as was trimellitic acid as described hereinbefore in Example 1 and the reaction mixture was otherwise treated as described therein.

In this manner, 95.3 kilograms of pyromellitic acid having an acid value of 880 (theoretical is 883), corresponding to a yield of 83.6% of the theoretical, was produced hourly together with 11.2 kilograms hourly of a residue consisting of a mixture of pyromellitic acid, of nitropyromellitic acid, dinitrophthalic acids, picric acid, and other by-products, corresponding to an hourly yield of 9.8% of the theoretical calculated as pyromellitic acid.

Figure 2:
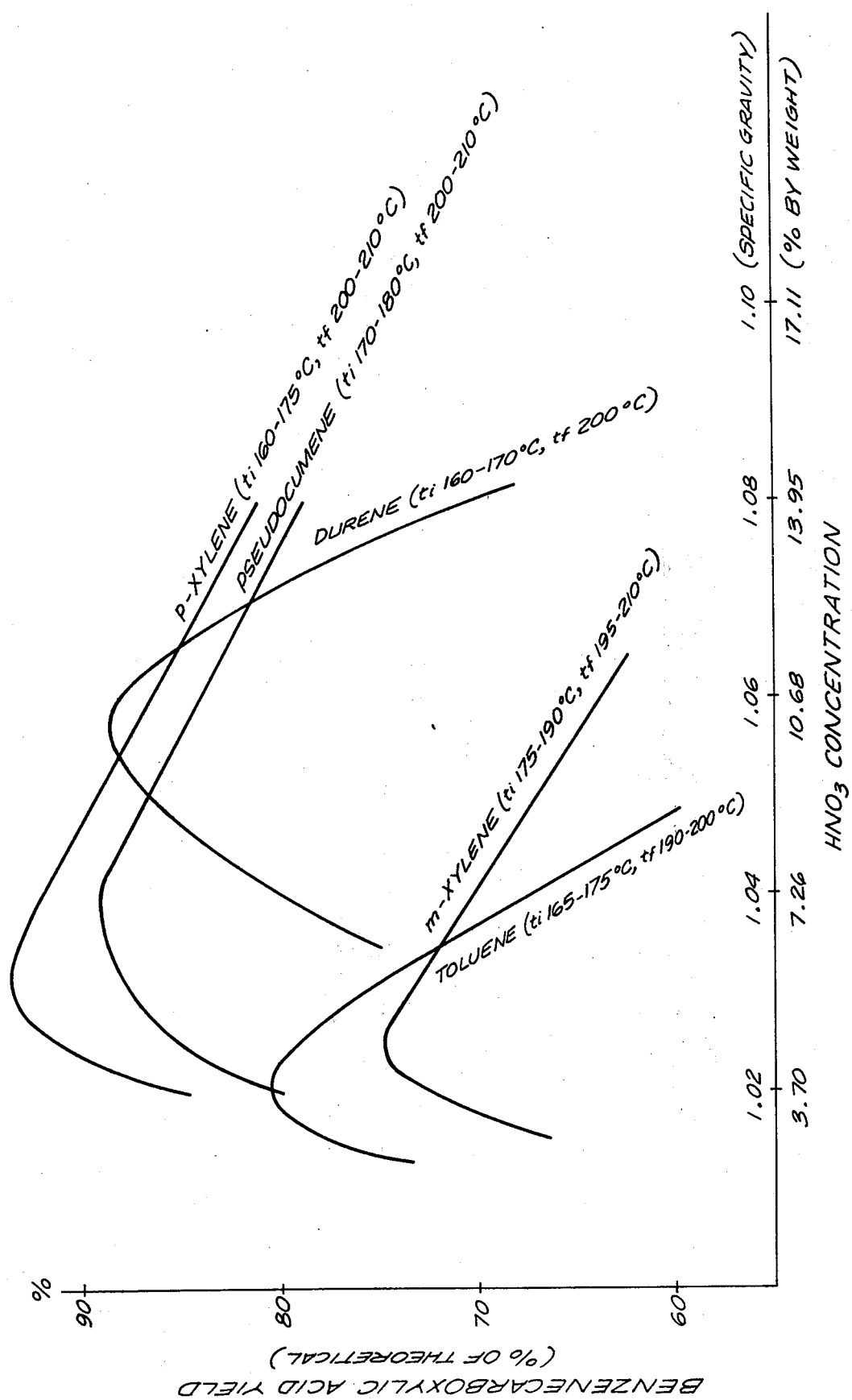
FIG. 2 of the drawings is a graphic representation of the effects of the nitric acid concentration upon the yields of the resulting benzenecarboxylic acid when various methyl-substituted benzenes are oxidized in accordance with the processes described herein.

The effect that the concentration of the nitric acid has on the yield of the benzenecarboxylic acid that is produced when methyl-substituted benzenes, specifically toluene, metaxylene, paraxylene, pseudocumene (1,2,4-trimethylbenzene), and durene (1,2,4,5-tetramethylbenzene) are oxidized in accordance with the processes described herein are represented in the respective graphs in FIG. 2 of the accompanying drawings. In these graphs, the yields of the benzenecarboxylic acids in terms of percentages of the theoretical yields are represented as ordinates while the abscissae represent specific gravity and concentration of the nitric acid in percentages by weight. All oxidations that are represented in the graphs were conducted as described herein and at superatmospheric pressures between 20 and 25 atmospheres and at the temperatures specified on each of the curves. The temperature at which the reaction mixtures were maintained in the first six of the reactor columns 1 to 6 that are referred to in FIG. 1 and in the Examples hereinbefore are referred to by the symbol $ti$ whereas the temperatures at which the reaction was maintained in the final reactor column 7 is referred to by the symbol $tf$.

From these curves it can be seen that the highest yield of the benzenecarboxylic acid is obtained within a narrow range. At nitric acid concentrations either higher or lower than the optimal, the yields in all cases decrease sharply. From this it is apparent that the nitric acid concentration must be continuously maintained at an optimal level and must not be allowed to vary widely while the oxidation of the aromatic compound is proceeding. Furthermore, it is to be noted that the optimal nitric acid concentration is different for each aromatic compound and that such optimal concentrations, if not previously established, should be determined preliminarily for each aromatic compound that is to be oxidized.

In accordance with these graphs it is to be noted that the best yields of benzoic acid from toluene are obtained when the concentration of the nitric acid is between 3 and 4% by weight and that the best yields of benzenecarboxylic acids are obtained from metaxylene when the nitric acid concentration is between 4 and 5%; from pseudocumene, between 6.5 and 7.5%; from paraxylene between 5 and 6%; and from durene, between 10 and 11%, all percentages being by weight.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a process for the continuous production of pyromellitic acid by reaction of durene with nitric acid, the improvement which comprises passing a reaction mixture consisting of durene and nitric acid having a concentration between 10 and 11% by weight of nitric acid through a series of seven consecutively interconnected vertical reactor columns in each of which the ratio of the weight of the reaction mixture containing the dilute nitric acid to the weight of durene is continuously maintained at at least 50:1, the nitric acid concentration in each of the reactor columns is maintained at the originally preselected concentration by the addition of amounts of more-concentrated nitric acid thereto while aliquot portions of durene are continuously introduced into each of the reactor columns to maintain the preselected ratio of nitric acid to durene, the first six of the said reactor columns being maintained at a temperature of 170°C and the final seventh column being maintained at a temperature of 200°C, and continuously discharging the reaction mixture containing between 10 and 20% by weight of pyromellitic acid thus produced from the final reactor column.

* * * * *